United States Patent
Gupta et al.

(10) Patent No.: US 9,228,214 B2
(45) Date of Patent: Jan. 5, 2016

(54) PROCESS FOR THE ENANTIOSELECTIVE ENZYMATIC REDUCTION OF HYDROXY KETO COMPOUNDS

(71) Applicant: CAMBREX IEP GMBH, Wiesbaden (DE)

(72) Inventors: Antje Gupta, Wiesbaden (DE); Maria Dupont, Huerth (DE); Anke Tschentscher, Eltville-Hattenheim (DE)

(73) Assignee: CAMBREX IEP GMBH, Wiesbaden (DE)

( * ) Notice: Subject to any disclaimer, the term of this patent is extended or adjusted under 35 U.S.C. 154(b) by 0 days.

(21) Appl. No.: 14/613,863

(22) Filed: Feb. 4, 2015

(65) Prior Publication Data

US 2015/0152451 A1    Jun. 4, 2015

Related U.S. Application Data

(62) Division of application No. 12/086,704, filed as application No. PCT/EP2006/012037 on Dec. 14, 2006, now Pat. No. 8,980,592.

(30) Foreign Application Priority Data

Dec. 19, 2005    (AT) .................................. 2027/2005

(51) Int. Cl.
   C12P 7/62        (2006.01)
   C12P 41/00       (2006.01)
   C12N 9/02        (2006.01)
   C12P 13/00       (2006.01)

(52) U.S. Cl.
   CPC ............... C12P 13/002 (2013.01); C12P 7/62 (2013.01); C12P 41/002 (2013.01); C12N 9/0008 (2013.01)

(58) Field of Classification Search
   CPC ........ C12P 7/62; C12P 13/002; C12P 41/002; C12N 9/0008
   USPC ......................................... 435/157, 135, 189
   See application file for complete search history.

(56) References Cited

U.S. PATENT DOCUMENTS

| | | | |
|---|---|---|---|
| 6,001,615 | A | 12/1999 | Reeve |
| 6,645,746 | B1 | 11/2003 | Kizaki et al. |
| 7,575,909 | B2 | 8/2009 | Gupta et al. |

FOREIGN PATENT DOCUMENTS

| | | |
|---|---|---|
| EP | 0569998 | 11/1993 |
| EP | 1152054 A1 | 11/2001 |
| WO | WO 01/85975 | 11/2001 |
| WO | WO 03/078615 A1 | 9/2003 |
| WO | WO 2004/111083 A2 | 12/2004 |
| WO | WO 2005/108593 A1 | 11/2005 |

OTHER PUBLICATIONS

Chica et al. "Semi-rational approaches to engineering enzyme activity: combining the benefits of directed evolution and rational design", Curr Opin Biotechnol. Aug. 2005; 16(4): 378-84.
Copeland et al., "Complete sequence of Rubrobacter xylanophilus DSM 9941", XP-002429149, Q1AU84__RUBXD, Q1AU84, Jul. 11, 2006.
Copeland et al., "Sequencing of the draft genome and assembly of Chloroflexus aurantiacus J-10-fl", Submitted Sep. 2005 to the EMBL GenBank DDBJ databases, Q3E5G4__CHLAU, Q3E5G4, XP-002429151, Nov. 22, 2005.
Oppermann et al., "Forms and functions of human SDR enzymes", Chemico-Biological Interactions 130-132 (2001) p. 699-705.
Sambrook and Russel, "Molecular Cloning: A Laboratroy Manual", Cold Spring Harbor Laboratory Press, Cold Spring Harbor, NY, USA, vol. 1, Third Edition, 2001. p. 1.132-142.
Sambrook and Russel, "Molecular Cloning: A Laboratroy Manual", Cold Spring Harbor Laboratory Press, Cold Spring Harbor, NY, USA, vol. 1, Third Edition, 2001. p. A8.9-1 0.
Takami et al., "Thermoadaptation trait revealed by the genome sequence of thermophylic Geobacillus kaustophilus", Q5KZB8__GEOKA, Q5KZB8, XP-002429150, Feb. 1, 2005, Nucleic Acids Res., 32: 6292-6303 (2004).
Witkowski et al., "Conversion of a •-ketoacyl synthase to a malonyl decarboxylase by replacement of the active-site cysteine with glutamine", Biochemistry 38:11643-11650, 1999.

*Primary Examiner* — Tekchand Saidha
*Assistant Examiner* — Md. Younus Meah
(74) *Attorney, Agent, or Firm* — Birch, Stewart, Kolasch & Birch, LLP.

(57) ABSTRACT

In a process for the enantioselective enzymatic reduction of a hydroxy ketone of general formula I

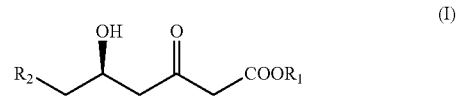

wherein $R_1=C_1-C_6$ alkyl and $R_2=$ —Cl, —CN, —OH, —H or $C_1-C_6$ alkyl, into a chiral diol of general formula II

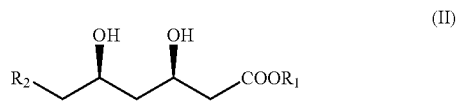

wherein $R_1$ and $R_2$ have the same meaning as in formula I, the hydroxy ketone is reduced with an oxidoreductase in the presence of NADH or NADPH as a cofactor, wherein
a) the hydroxy ketone is provided in the reaction at a concentration of $\geq 50$ g/l,
b) the oxidized cofactor NAD or NADP having formed is regenerated continuously by oxidation of a secondary alcohol of general formula $R_XR_Y$CHOH, wherein $R_X$, $R_Y$ independently represent hydrogen, branched or unbranched $C_1$-$C_8$-alkyl and $C_{total} \geq 3$, and
c) the reduction of the hydroxy ketone and the oxidation of the secondary alcohol are catalyzed by the same oxidoreductase.

13 Claims, No Drawings

PROCESS FOR THE ENANTIOSELECTIVE ENZYMATIC REDUCTION OF HYDROXY KETO COMPOUNDS

CROSS REFERENCE TO RELATED APPLICATIONS

This application is a Divisional Application of co-pending U.S. application Ser. No. 12/086,704 filed Nov. 10, 2008, now U.S. Pat. No. 8,980,592 which is the National Phase of PCT/EP2006/012037 filed on Dec. 14, 2006, which claims priority to Patent Application No. 2027/2005 filed in Austria on Dec. 19, 2005, all of which are hereby expressly incorporated by reference into the present application.

The invention relates to a process for the enantioselective enzymatic reduction of a hydroxy ketone of general formula I

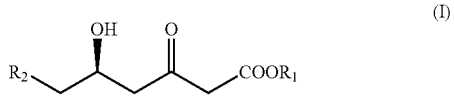

wherein $R_1 = C_1$-$C_6$ alkyl and $R_2 = $ —Cl, —CN, —OH, —H or $C_1$-$C_6$ alkyl, into a chiral diol of general formula II

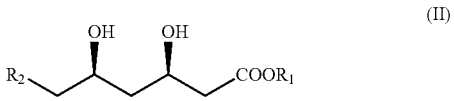

wherein $R_1$ and $R_2$ have the same meaning as in formula I, with the hydroxy ketone being reduced with an oxidoreductase in the presence of a cofactor.

Chiral diols of general formula II are important intermediates in the production of pharmaceutical products, in particular in the production of HMG-CoA reductase inhibitors. Such chiral diols are, for example, tert. butyl (3R,5S)-6-chloro-3,5-dihydroxyhexanoate, tert. butyl (3R,5R)-6-cyano-3,5-dihydroxyhexanoate or tert. butyl (5S,3R)-3,5,6-trihydroxyhexanoate.

Diols of this kind are produced in particular by enantioselective reduction of the corresponding hydroxy ketones of formula I such as, e.g., tert. butyl (5R)-6-cyano-5-hydroxy-3-oxohexanoate, tert. butyl (5S)-6-chloro-5-hydroxy-3-oxohexanoate or tert. butyl (5S)-5,6-dihydroxy-3-oxohexanoate. In doing so, the chemically catalyzed reduction has the disadvantage that, on the one hand, it may result in byproducts due to the harsh reaction conditions and, on the other hand, yields unsatisfactory enantiomeric and diastereomeric excesses, respectively, and is technically feasible only with very large efforts.

For this reason, there have, for quite some time, been endeavors to develop biocatalytic processes which allow for the enantioselective reduction of the above-mentioned hydroxy ketones. Biocatalytic processes usually operate under mild conditions, which is why they can be expected to enable the reduction of 5-hydroxy-3-oxohexanoate derivatives, which are rather unstable anyway, without the formation of further byproducts. So far, however, it has not been possible to find any suitable biocatalysts by means of which the enzymatic reduction of the above-mentioned 5-hydroxy-3-oxohexanoate derivatives is feasible in an effective manner and with isolated enzymes.

For instance, the U.S. Pat. No. 6,001,615 and the international patent application WO 01/85975 A1 describe the reduction of tert. butyl (5R)-6-cyano-5-hydroxy-3-oxohexanoate and of tert. butyl (5S)-5,6-dihydroxy-3-oxohexanoate, respectively, with various yeasts of the genus *Beauvaria, Pichia, Candida, Kluyveromyces* and *Torulaspora*. Thereby, however, the conversions occur only with whole cells of wild strains and therefore can only be carried out at very low concentrations of far below 5%. So far, it has not yet been possible to identify the enzymes and DNA sequences responsible for the conversions.

Furthermore, microbial conversions of structurally similar compounds are described in EP 0 569 998 B1. Therein, it has even been possible to purify an NADH-dependent enzyme from *Acinetobacter calcoaceticus* ATCC 33305, which is also used in an isolated state together with glucose dehydrogenase for coenzyme regeneration. In the process described, the substrate is used at concentrations of 1% and a "total turn over number" of the NADH of merely 10 is achieved. An industrially applicable process has not been presented.

In the U.S. Pat. No. 6,645,746 B1, an amino acid sequence from *Candida magnoliae* is disclosed, which may be used for reducing tert. butyl (5S)-6-chloro-5-hydroxy-3-oxohexanoate to tert. butyl (3R,5S)-6-chloro-3,5-dihydroxyhexanoate with the aid of NADPH. In the specification of said document, the enzyme is preferably used in a state in which it is coexpressed with glucose dehydrogenase from *Bacillus megaterium*, wherein the regeneration of cofactor NADPH occurs with the aid of the glucose dehydrogenase and with glucose as a cosubstrate.

It is the object of the invention to provide a process which enables the economical production of enantiomerically pure diols of general formula II in high yields and with high enantiomeric purity without any byproducts.

According to the invention, this object is achieved by a process of the initially mentioned kind, wherein the oxidoreductase is reduced in the presence of NADH or NADPH as a cofactor and which is characterized in that a) the hydroxy ketone is provided in the reaction at a concentration of ≥50 g/l, b) the oxidized cofactor NAD or NADP having formed is regenerated continuously by oxidation of a secondary alcohol of general formula $R_X R_Y$CHOH, wherein $R_X$, $R_Y$ independently represent hydrogen, branched or unbranched $C_1$-$C_8$-alkyl and $C_{total} \geq 3$, and c) the reduction of the hydroxy ketone and the oxidation of the secondary alcohol are catalyzed by the same oxidoreductase.

A preferred embodiment of the process is characterized in that the oxidoreductase a) comprises an amino acid sequence in which at least 50% of the amino acids are identical to those of amino acid sequence SEQ ID NO:1, SEQ ID NO:8, SEQ ID NO:11 or SEQ ID NO:14, b) is encoded by the nucleic acid sequence SEQ ID NO:2, SEQ ID NO:3, SEQ ID NO:9, SEQ ID NO:10, SEQ ID NO:12, SEQ ID NO:13 or SEQ ID NO:15, or c) is encoded by a nucleic acid sequence which hybridizes to SEQ ID NO:2, SEQ ID NO:3, SEQ ID NO:9, SEQ ID NO:10, SEQ ID NO:12, SEQ ID NO:13 or SEQ ID NO:15 under stringent conditions.

According to the invention, the above-mentioned object is also achieved by a process of the initially mentioned kind, wherein the oxidoreductase a) comprises an amino acid sequence in which at least 50% of the amino acids are identical to those of amino acid sequence SEQ ID NO:1, SEQ ID NO:8, SEQ ID NO:11 or SEQ ID NO:14, b) is encoded by the nucleic acid sequence SEQ ID NO:2, SEQ ID NO:3, SEQ ID NO:9, SEQ ID NO:10, SEQ ID NO:12, SEQ ID NO:13 or SEQ ID NO:15, or c) is encoded by a nucleic acid sequence which hybridizes to SEQ ID NO:2, SEQ ID NO:3, SEQ ID NO:9, SEQ ID NO:10, SEQ ID NO:12, SEQ ID NO:13 or SEQ ID NO:15 under stringent conditions.

It has been found that the polypeptides comprising amino acid sequences SEQ ID NO:1, SEQ ID NO:8 and SEQ ID NO:11 show oxidoreductase activity and can be used for reducing tert. butyl (5R)-6-cyano-5-hydroxy-3-oxohexanoate with a diastereomeric excess of >99% to tert. butyl (3R,5R)-6-cyano-3,5-dihydroxyhexanoate. Other hydroxy ketones of general formula I can be reduced in the same manner by means of amino acid sequences SEQ ID NO:1, SEQ ID NO:8 and SEQ ID NO:11.

In addition, the aforementioned oxidoreductases have the advantage of being able to regenerate the oxidized cofactor that is formed during the reduction by reducing a secondary alcohol. Thus, a particular economic advantage of said oxidoreductases also consists in that, in contrast to processes of the prior art (U.S. Pat. No. 6,645,746 B and EP 0 569 998 B), no further enzyme is required for cofactor regeneration.

A DNA sequence SEQ ID NO:2, which codes for a polypeptide comprising SEQ ID NO:1, is obtainable, for example, from the genome of the organism *Rubrobacter xylanophilus* DSM 9941. In addition, it has been found that the DNA sequence SEQ ID NO:3 can be used for expressing the polypeptide of SEQ ID NO:1 in *Escherichia*.

A DNA sequence SEQ ID NO:9, which codes for a polypeptide comprising SEQ ID NO:8, is obtainable, for example, from the genome of the organism *Geobacillus thermodenitrificans* DSM 465. In addition, it has been found that the DNA sequence SEQ ID NO:10 can be used for expressing the polypeptide of SEQ ID NO:8 in *Escherichia*.

A DNA sequence SEQ ID NO:12, which codes for a polypeptide comprising SEQ ID NO:11, is obtainable, for example, from the genome of the organism *Chloroflexus aurantiacus* DSM 635.

A DNA sequence SEQ ID NO:15, which codes for a polypeptide comprising SEQ ID NO:14, is obtainable, for example, from the organism *Candida magnoliae* CBS 6396.

Thus, the present invention also relates to a process for the reduction of hydroxy ketones of general formula I into diols of general formula II, using a polypeptide comprising amino acid sequence SEQ ID NO:1, SEQ ID NO:8, SEQ ID NO:11 or SEQ ID NO:14, or a polypeptide which comprises an amino acid sequence which is identical by at least 50% to the amino acid sequence SEQ ID NO:1, SEQ ID NO:8, SEQ ID NO:11 or SEQ ID NO:14, i.e., a polypeptide which can be derived by substitution, insertion, deletion or addition from at least one amino acid of SEQ ID NO:1, SEQ ID NO:8, SEQ ID NO:11 or SEQ ID NO:14, or using a polypeptide which is encoded by the nucleic acid sequence SEQ ID NO:2, SEQ ID NO:9, SEQ ID NO:12 or SEQ ID NO:15 or by a nucleic acid sequence which hybridizes to SEQ ID NO:2, SEQ ID NO:9, SEQ ID NO:12 or SEQ ID NO:15 under stringent conditions.

By a nucleic acid sequence which hybridizes, for example, to SEQ ID NO:2 under stringent conditions, a polynucleotide is understood which can be identified via the colony hybridization method, the plaque hybridization method, the Southern hybridization method or comparable methods, using SEQ ID NO:2 as a DNA probe.

For this purpose, the polynucleotide immobilized on a filter is hybridized, for example, to SEQ ID NO:2 in a 0.7-1 M NaCl solution at 60° C. Hybridization is carried out as described, for instance, in Molecular Cloning, A Laboratory Manual, Second Edition (Cold Spring Harbor Laboratory Press, 1989) or in similar publications. Subsequently, the filter is washed with a 0.1 to 2-fold SSC solution at 65° C., wherein a 1-fold SSC solution is understood to be a mixture consisting of 150 mM NaCl and 15 mM sodium citrate.

In the process according to the invention, the polypeptide comprising the sequence SEQ ID NO:1, SEQ ID NO:8, SEQ ID NO:11 or SEQ ID NO:14 and polypeptides derivable from said polypeptides, respectively, can be used either in a completely purified state, in a partially purified state or as cells containing the polypeptide SEQ ID NO:1, SEQ ID NO:8, SEQ ID NO:11 or SEQ ID NO:14. Thereby, the cells used can be provided in a native, permeabilized or lysed state. Preferably, the polypeptide comprising the sequence SEQ ID NO:1, SEQ ID NO:8, SEQ ID NO:11 or SEQ ID NO:14 and derivatives derivable therefrom, respectively, are overexpressed in a suitable host organism such as, for example, *Escherichia coli*, and the recombinant polypeptide is used for reducing the hydroxy ketone of general formula I.

5.000 to 10 Mio U of oxidoreductase SEQ ID NO:1, SEQ ID NO:8, SEQ ID NO:11 or SEQ ID NO:14 or derivatives thereof, respectively, are used per kg of the compound of Formula I to be reacted (upwardly open). Herein, the enzyme unit 1 U corresponds to the enzyme amount which is required for reacting 1 µmol of the hydroxy ketone of formula I per minute (min).

The enzymatic reduction according to the invention proceeds under mild conditions so that the degradation of the frequently unstable hydroxy ketone and thus the formation of undesired byproducts can be largely avoided. The process according to the invention has a high service life and a diastereomeric purity of normally >99% of the chiral diols produced.

A preferred embodiment of the invention is characterized in that the cofactor used in the process is continuously reduced with a cosubstrate. Preferably, NAD(P)H is used as the cofactor, with the NAD(P) formed in the reduction again being reduced to NAD(P)H by means of the cosubstrate.

Secondary alcohols such as 2-propanol, 2-butanol, 2-pentanol, 3-pentanol, 4-methyl-2-pentanol, 2-heptanol, 2-octanol or cyclohexanol are thereby preferably used as cosubstrates. According to a particularly preferred embodiment, 2-propanol is used for coenzyme regeneration. The amount of cosubstrate for the regeneration can range from 5 to 95% by volume, based on the total volume.

Coenzyme regeneration is, for example, likewise effected via the polypeptide comprising SEQ ID NO:1, SEQ ID NO:8, SEQ ID NO:11 or SEQ ID NO:14.

In the process according to the invention, the hydroxy ketone of general formula I is preferably used in an amount of from 5 to 50% by weight (50 g/1 to 50 g/1), based on the total volume, preferably from 8 to 40% by weight, in particular from 10 to 25% by weight.

A particularly preferred embodiment is characterized in that tert. butyl (5R)-6-cyano-5-hydroxy-3-oxohexanoate, tert. butyl (5S)-6-chloro-5-hydroxy-3-oxohexanoate or tert. butyl (5S)-5,6-dihydroxy-3-oxohexanoate is used as the hydroxy ketone of general formula (I).

Preferably, the process according to the invention is carried out in an aqueous organic two-phase system.

The aqueous portion of the reaction mixture in which the enzymatic reduction proceeds preferably contains a buffer, e.g., a potassium phosphate, tris/HCl or triethanolamine buffer, having a pH value of from 5 to 10, preferably a pH of from 6 to 9. In addition, the buffer can contain ions for stabilizing or activating the enzymes such as, for example, zinc ions or magnesium ions.

While carrying out the process according to the invention, the temperature suitably ranges from about 10° C. to 70° C., preferably from 20° C. to 45° C.

In a further preferred embodiment of the process according to the invention, the enzymatic conversion is carried out in the presence of an organic solvent which is not miscible with water or is miscible with water only to a limited degree. Said solvent is, for example, a symmetric or unsymmetric di($C_1$-$C_6$)alkyl ether, a linear-chain or branched alkane or cycloalkane or a water-insoluble secondary alcohol which, at the same time, represents the cosubstrate. The preferred organic solvents are diethyl ether, tertiary butyl methyl ether, diisopropyl ether, dibutyl ether, butyl acetate, heptane, hexane, 2-octanol, 2-heptanol, 4-methyl-2-pentanol and cyclohexanol. In case of the last-mentioned secondary alcohols, the solvent can simultaneously also serve as a cosubstrate for cofactor regeneration.

If water-insoluble solvents and cosubstrates, respectively, are used, the reaction batch consists of an aqueous phase and an organic phase. According to its solubility, the hydroxy ketone is distributed between the organic phase and the aqueous phase. In general, the organic phase has a proportion of from 5 to 95%, preferably from 10 to 90%, based on the total reaction volume. The two liquid phases are preferably mixed mechanically so that, between them, a large surface area is generated. Also in this embodiment, the NAD formed in the enzymatic reduction, for example, can again be reduced to NADH with a cosubstrate, such as described above.

The concentration of the cofactor, in particular of NADH or NADPH, respectively, in the aqueous phase generally ranges from 0.001 mM to 10 mM, in particular from 0.01 mM to 1 mM.

In the process according to the invention, a stabilizer of oxidoreductase/dehydrogenase can also be used. Suitable stabilizers are, for example, glycerol, sorbitol, 1,4-DL-dithiothreitol (DTT) or dimethyl sulfoxide (DMSO).

The process according to the invention is carried out, for example, in a closed reaction vessel made of glass or metal. For this purpose, the components are transferred individually into the reaction vessel and stirred under an atmosphere of, e.g., nitrogen or air.

According to another possible embodiment of the invention, the oxidized cosubstrate (e.g. acetone) can be removed continuously and/or the cosubstrate (e.g. 2-propanol) can be newly added in a continuous manner in order to shift the reaction equilibrium towards the reaction product (diol of general formula II).

In a further embodiment, the addition of the oxidoreductase according to SEQ ID NO:1, SEQ ID NO:8, SEQ ID NO:11 or SEQ ID NO:14 and/or of the cosubstrate can also be effected gradually in the course of the process.

After completion of the reduction, the reaction mixture is processed. For this purpose, the aqueous phase is optionally separated from the organic phase and the organic phase containing the product is filtered. Optionally, the aqueous phase can also be extracted and processed further like the organic phase. Thereupon, the solvent is evaporated from the organic phase and the diol of general formula II is obtained as a crude product. The crude product can then be purified further or used directly for the synthesis of a follow-up product.

In the following, the invention is illustrated further by way of examples.

Example 1

Cloning of oxidoreductase from *Rubrobacter xylanophilus* DSM 9941

A) Cultivation of *Rubrobacter xylanophilus* DSM 9941

Cells of *Rubrobacter xylanophilus* DSM 9941 were cultivated in the following medium at 50° C. (pH 7.2) and 140 rpm in a bacterial shaker: 0.1% yeast extract, 0.1% tryptone, 0.004% $CaSO_4 \times 2 H_2O$, 0.02% $MgCl_2 \times 6 H_2O$, 0.01% nitrilotriacetic acid, 100 ml phosphate buffer [5.44 g/l $KH_2PO_4$, 43 g/l $Na_2HPO_4 \times 12 H_2O$], 500 µl/10.01 M Fe citrate, 500 µl/l trace element [500 µl/l $H_2SO_4$, 2.28 g/l $MnSO_4 \times H_2O$, 500 mg/l $ZnSO_4 \times 7 H_2O$, 500 mg $H_3BO_3$, 25 mg/l $CuSO_4 \times 5 H_2O$, 25 mg/l $Na_2MoO_4 \times 2 H_2O$, 45 mg/l $CoCl_2 \times 6 H_2O$]. On day 6 of the cultivation, cells were separated from the culture medium by centrifugation and stored at −80° C.

B) Amplification of the Gene Coding for Selective Oxidoreductase

Genomic DNA was extracted according to the method described in "Molecular Cloning" by Manniatis & Sambrook. The resulting nucleic acid served as a template for the polymerase chain reaction (PCR) involving specific primers which were derived from the gene sequence published under number 46106817 in the NCBI database. In doing so, the primers were provided in a 5'-terminal position with restriction sites for the endonucleases Nde I and Hind III or Sph I, respectively (SEQ ID NO:4, SEQ ID NO:5, SEQ ID NO:7), for subsequent cloning into an expression vector.

Amplification was carried out in a PCR buffer [10 mM tris-HCl, (pH 8.0); 50 mM KCl; 10 mM $MgSO_4$; 1 mM dNTP Mix; per 20 pMol of primer and 2.5 U of Platinum Pfx DNA polymerase (Invitrogen)] with 500 ng of genomic DNA and the following temperature cycles:

Cycle 1: 94° C., 2 min
Cycle 2×30: 94° C., 15 sec
  54° C., 30 sec
  68° C., 60 sec
Cycle 3: 68° C., 7 min
  4° C., ∞

The resulting PCR product having a size of about 750 bp was restricted after purification over a 1% agarose gel with the aid of the endonucleases Nde I and Hind III or Sph I and Hind III, respectively, and was ligated into the backbone of the pET21a vector (Novagen) or of the pQE70 vector (Qiagen), respectively, which backbone had been treated with the same endonucleases. After transforming 2 µl of the ligation batch into *E. coli* Top 10 F' cells (Invitrogen), plasmid DNA of ampicillin-resistant colonies was tested for the presence of an insert having a size of 750 bp by means of a restriction analysis with the endonucleases Nde I and Hind III or Sph I and Hind III, respectively. Plasmid preparations from the clones which were positive for the fragment were subjected to a sequence analysis and subsequently transformed into *Escherichia coli* BL21 Star (Invitrogen) and *E. coli* RB791 (genetic stock, Yale), respectively.

Example 2

Efficient Expression of Polypeptide SEQ ID NO:1 in *Escherichia coli* Cells

In order to obtain efficient expression of the polypeptide SEQ ID NO:1 in *Escherichia coli* cells, for cloning into an expression vector coding DNA SEQ ID NO:3 was used as a template in a PCR reaction. In the region of the first 160 base pairs, this DNA sequence differed in 51 bases from the previously known DNA sequence (SEQ ID NO:2). This modification was conservative and did not result in a change in the amino acid sequence.

Amplification was carried out in a PCR buffer [10 mM tris-HCl, (pH 8.0); 50 mM KCl; 10 mM MgSO$_4$; 1 mM dNTP Mix; per 20 pMol of primer (SEQ ID NO:6, SEQ ID NO:5) and 2.5 U of Platinum Pfx DNA polymerase (Invitrogen)] with 50 ng of DNA SEQ ID NO:3 as a template and the following temperature cycles:
Cycle 1: 94° C., 2 min
Cycle 2×30: 94° C., 40 sec
  56° C., 30 sec
  68° C., 60 sec
Cycle 3: 68° C., 7 min
  4° C., ∞

The resulting PCR product having a size of about 750 bp was ligated after purification over a 1% agarose gel with the aid of the endonucleases Nhe I and Hind III into the backbone of the pET21a vector (Novagen), which backbone had been treated with the same endonucleases. After transforming 2 µl of the ligation batch into *E. coli* Top 10 F' cells (Invitrogen), plasmid DNA of ampicillin-resistant colonies was tested for the presence of an insert having a size of 750 bp by means of a restriction analysis with the endonucleases Nhe I and Hind III. Plasmid preparations from the clones which were positive for the fragment were subjected to a sequence analysis and subsequently transformed into *Escherichia coli* BL21 Star (Invitrogen).

Example 3

Preparation of Oxidoreductase from *Rubrobacter xylanophilus* DSM 9941

The *Escherichia coli* strains BL21 Star (Invitrogen, Karlsruhe, Germany) and RB791 (*E. coli* genetic stock, Yale, USA), respectively, which had been transformed with the expression construct, were cultivated in a medium (1% tryptone, 0.5% yeast extract, 1% NaCl) with ampicillin (50 µg/ml) until an optical density of 0.5, measured at 550 nm, was reached. The expression of recombinant protein was induced by adding isopropylthiogalactoside (IPTG) at a concentration of 0.1 mM. 16 hours after the induction at 25° C. and 220 rpm, the cells were harvested and frozen at −20° C.

For enzyme recovery, 30 g cells were suspended in 150 ml of triethanolamine buffer (100 mM, pH=7, 2 mM MgCl$_2$, 10% glycerol) and broken down by means of a high-pressure homogenizer. Subsequently, the enzyme solution was mixed with 150 ml of glycerol and stored at −20° C.

The enzyme solution thus obtained was used for the synthesis of tert. butyl (3R,5R)-6-cyano-3,5-dihydroxyhexanoate.

In the diluted state, the enzyme solution obtained was also used for the corresponding enzymatic measurements. Thereby, the activity test was made up of the following: 870 µl of 100 mM TEA buffer, pH 7.0, 160 µg NAD(P)H, 10 µl diluted cell lysate. The reaction was initiated by adding 100 µl of the 100 mM substrate solution tert. butyl (5R)-6-cyano-5-hydroxy-3-oxohexanoate to the reaction mixture.

Example 4

Conversion of tert. butyl (5R)-6-cyano-5-hydroxy-3-oxohexanoate into tert. butyl (3R,5R)-6-cyano-3,5-dihydroxyhexanoate by means of oxidoreductase SEQ ID NO:1

For the conversion of tert. butyl (5R)-6-cyano-5-hydroxy-3-oxohexanoate into tert. butyl (3R,5R)-6-cyano-3,5-dihydroxyhexanoate, a mixture of 900 µl buffer (100 mM TEA, pH=7, 1 mM MgCl$_2$), 100 µl 2-propanol, 10 µl tert. butyl (5R)-6-cyano-5-hydroxy-3-oxohexanoate crude product (enantiomeric purity>99%), 0.1 mg NAD and 100 µl enzyme suspension (see Example 3) was incubated in an Eppendorf reaction vessel for 24 h at room temperature, under continual mixing. After 24 h, 96% of the tert. butyl (5R)-6-cyano-5-hydroxy-3-oxohexanoate used had been reduced to tert. butyl (3R,5R)-6-cyano-3,5-dihydroxyhexanoate. The diastereomeric excess amounted to >99%.

The determination of the conversion as well as of the diastereomeric excess was performed by chiral gas chromatography. For this purpose, a gas chromatograph GC-17A from Shimadzu comprising a chiral separating column CP-Chirasil-DEX CB (Varian Chrompack, Darmstadt, Germany), a flame ionization detector and helium as a carrier gas was used.

The separation of tert. butyl-6-cyano-3,5-dihydroxyhexanoate occurred at 0.72 bar and for 10 min at 50° C., 5° C./min→200° C. for 10 min.

The retention times were: (R—BCH) 4.4 min; (R,R—BCH) 47.1 min and (R,S—BCH) 48.2 min.

Example 5

Synthesis of tert. butyl (3R,5R)-6-cyano-3,5-dihydroxyhexanoate from tert. butyl (5R)-6-cyano-5-hydroxy-3-oxohexanoate by means of oxidoreductase SEQ ID NO:1

For a further conversion of tert. butyl (5R)-6-cyano-5-hydroxy-3-oxohexanoate into tert. butyl (3R,5R)-6-cyano-3,5-dihydroxyhexanoate, a mixture of 550 µl buffer (100 mM TEA, pH=7, 1 mM MgCl$_2$), 150 µl 2-propanol, 200 µl tert. butyl (5R)-6-cyano-5-hydroxy-3-oxohexanoate crude product (enantiomeric purity>99%), 0.1 mg NAD and 200 µl enzyme suspension (see Example 3) was incubated in an Eppendorf reaction vessel. In the course of the reaction, the acetone/2-propanol mixture formed was evaporated repeatedly by the introduction of nitrogen, and fresh 2-propanol and 50 µl of enzyme were added. After 2 to 3 repeats at 24-hour intervals, >90% of the tert. butyl (5R)-6-cyano-5-hydroxy-3-oxohexanoate used had been reduced to tert. butyl (3R,5R)-6-cyano-3,5-dihydroxyhexanoate. The diastereomeric excess amounted to >99%.

Example 6

Synthesis of tert. butyl (3R,5R)-6-cyano-3,5-dihydroxyhexanoate from tert. butyl (5R)-6-cyano-5-hydroxy-3-oxohexanoate by means of oxidoreductase SEQ ID NO:1

For a further conversion of tert. butyl (5R)-6-cyano-5-hydroxy-3-oxohexanoate into tert. butyl (3R,5R)-6-cyano-3,5-dihydroxyhexanoate, a mixture of 6.7 ml buffer (100 mM TEA, pH=9), 1.7 ml 2-propanol, 2 ml tert. butyl (5R)-6-cyano-5-hydroxy-3-oxohexanoate crude product (enantiomeric purity>99%), 1.0 mg NAD and 150 mg frozen cells *E. coli* BL21 Star, containing oxidoreductase SEQ ID NO:1, (see Example 3) was incubated in a reaction vessel at 45° C. After 24 h, >90% of the tert. butyl (5R)-6-cyano-5-hydroxy-3-oxohexanoate used had been reduced to tert. butyl (3R,5R)-6-cyano-3,5-dihydroxyhexanoate. The diastereomeric excess amounted to >99%.

Example 7

Synthesis of tert. butyl (3R,5R)-6-cyano-3,5-dihydroxyhexanoate from tert. butyl (5R)-6-cyano-5-hydroxy-3-oxohexanoate by means of oxidoreductase SEQ ID NO:8

For a further conversion of tert. butyl (5R)-6-cyano-5-hydroxy-3-oxohexanoate into tert. butyl (3R,5R)-6-cyano-3,5-dihydroxyhexanoate, a mixture of 5.0 ml buffer (100 mM TEA, pH=7.5), 2.0 ml 2-propanol, 4.0 ml tert. butyl (5R)-6-cyano-5-hydroxy-3-oxohexanoate crude product (enantiomeric purity>99%), 1.0 mg NAD and 250 mg frozen cells *E. coli* RB 791, containing oxidoreductase SEQ ID NO:8, (corresponding to Examples 2 and 3) was incubated in a reaction vessel at 40° C. After 24 h, >90% of the tert. butyl (5R)-6-cyano-5-hydroxy-3-oxohexanoate used had been reduced to tert. butyl (3R,5R)-6-cyano-3,5-dihydroxyhexanoate. The diastereomeric excess amounted to >99%.

Example 8

Synthesis of tert. butyl (3R,5R)-6-cyano-3,5-dihydroxyhexanoate from tert. butyl (5R)-6-cyano-5-hydroxy-3-oxohexanoate by means of oxidoreductase SEQ ID NO:11

For the conversion of tert. butyl (5R)-6-cyano-5-hydroxy-3-oxohexanoate into tert. butyl (3R,5R)-6-cyano-3,5-dihydroxyhexanoate, a mixture of 350 µl buffer (100 mM potassium phosphate, pH=7), 150 µl 2-propanol, 50 µl tert. butyl (5R)-6-cyano-5-hydroxy-3-oxohexanoate crude product (enantiomeric purity>99%), 0.025 mg NAD and 15 µl enzyme suspension SEQ ID NO:11 (see Example 3) was incubated in an Eppendorf reaction vessel for 48 h at room temperature, under continual mixing. After 48 h, >80% of the tert. butyl (5R)-6-cyano-5-hydroxy-3-oxohexanoate used had been reduced to tert. butyl (3R,5R)-6-cyano-3,5-dihydroxyhexanoate. The diastereomeric excess amounted to >99%.

```
Sequence listing
                                                                         SEQ ID NO: 1
  1 mlegkvavit gagsgigrat alrfaregar vvvaelderr
 41 geevvreile sggeavfvrt dvsefeqvea averaveeyg
 81 tldvmfnnag ighyaplleh dpehydrvvr vnqygvyygi
121 laagrkmael enpgviinta svyaflaspg vigyhaskga
161 vkmmtqaaal elaphgirvv aiapggvdtp iiqgykdmgl
201 gerlargqmr rrlqtpeqia gavvllatee adaingsvvm
241 tddgyaefk SEQ ID NO: 2
  1 atgctcgaggggaaggtcgcggtcatcacggggccggca
 41 gcggcataggccgggccaccgcgctcaggttcgcccgcga
 81 aggggcccgggtggtcgtggcggagctcgacgagcggagg
121 ggggaggaggtcgtccgggagatcctcgagtccggcgggg
161 aggccgtcttcgtgaggacggacgtctcggagttcgagca
201 ggttgaggccgccgtcgagcgcgccgtcgaggagtacggg
241 acgctggacgtcatgttcaacaacgccggcatcgggcact
281 acgccccctgctggagcacgacccggagcactacgaccg
321 ggtggtccgggtgaaccagtacggcgtctactacgggata
361 ctcgccgccggcaggaagatggccgagctggagaaccccg
401 gcgtgatcatcaacaccgcctcggtctacgctttcctggc
441 ctcccccggtgtgatcggctatcacgcttccaaggggggcg
481 gtgaagatgatgacccaggccgcagccctggagctcgcc
521 cccacggcatacgggtcgtcgccatcgcccccgggcggggt
561 ggacacccccgatcatccagggctacaaggacatgggcctc
601 ggtgagcggctggcccgcggccagatgcgtcgcaggctcc
641 agaccccgagcagatcgccggcgccgtcgtcctgctcgc
681 caccgaggaggcagacgccataaacgctcggtggtgatg
721 accgacgacggctacgcggagttcaagtaa SEQ ID NO: 3
  1 atgctggaag gtaaagtggc agtcatcacc ggtgcaggca
 41 gcggcattgg gcgtgccact gcgctgcgtt ttgcgcgtga
 81 aggcgctcgc gtcgttgtgg ccgagctgga tgaacgtcgc
121 ggtgaggaag ttgtacgtga gattctgaa tctggcgggg
161 gggaggccgt cttcgtgagg acggacgtct cggagttcga
201 gcaggttgag gccgccgtcg agcgcgccgt cgaggagtac
241 gggacgctgg acgtcatgtt caacaacgcc ggcatcgggc
281 actacgcccc cctgctggag cacgacccgg agcactacga
321 ccgggtggtc cgggtgaacc agtacggcgt ctactacggg
361 atactcgccg ccggcaggaa gatggccgag ctggagaacc
401 ccggcgtgat catcaacacc gcctcggtct acgctttcct
441 ggcctccccc ggtgtgatcg gctatcacgc ttccaagggg
481 gcggtgaaga tgatgaccca ggccgcagcc ctggagctcg
521 cccccccacgg catacgggtc gtcgccatcg ccccgggcgg
561 ggtggacacc ccgatcatcc agggctacaa ggacatgggc
601 ctcggtgagc ggctggcccg cggccagatg cgtcgcaggc
641 tccagacccc cgagcagatc gccggcgccg tcgtcctgct
681 cgccaccgag gaggcagacg ccataaacg ctcggtggtg
721 atgaccgacg acggctacgc ggagttcaag taa

SEQ ID NO: 4
GGGAATTCCATATGATGCTCGAGGGGAAGGTCG
```

-continued

```
                                                          SEQ ID NO: 5
CCCAAGCTTATTACTTGAACTCCGCGTAGCCGTC

SEQ ID NO: 6
CCTAGCTAGCATGCTGGAAGGTAAAGTGGC

SEQ ID NO: 7
CACATGCATGCGAATGCTCGAGGGGAAGGTC
```

Geobacillus thermodenitrificans DSM 465 protein sequence carbonyl reductase
SEQ ID NO: 8

```
  1 mrlkgkaaiv tggasgigra tairfaeega kvaysdinee ggeetvrlir ekggeaifvq
 61 tdvadskqvs rlvqtavdaf gglhilfnna gighsevrst dlseeewdry invnlkgvfl
121 gikyavpvmk qcgggaivnt ssllgikgkk yesaynaska gvilltknaa leygkfniry
181 naiapgvidt niitpwkqde rkwpiiskan algrigtpee vanavlflas deasfitgat
241 lsvdgggltf
```

Geobacillus thermodenitrificans DSM 465 nucleic acid sequence carbonyl reductase
SEQ ID NO: 9

```
  1 atgaggctaa aaggaaaagc ggcgattgtc accggcggcg cgagcggcat cggccgggcg
 61 acggcgattc gctttgcgga agaaggcgcc aaagtggcgg tgagcgacat caatgaggaa
121 ggaggggaag aaacggtccg cctgattcgg gaaaaaggag gggaggcgat ttttgtccaa
181 acggacgtag ccgattccaa gcaagtgagc cgccttgtcc aaacgcgcgt tgatgccttt
241 ggcggcctac atattctctt taacaatgcc ggcatcggcc attcggaagt gcggagcacc
301 gacttgtctg aagaagagtg ggaccgggtc atcaacgtta atttgaaagg agtgttcctt
361 ggcatcaaat acgcggtgcc cgtgatgaag caatgcggtg gcggggccat tgtcaacaca
421 tcgagcctgc ttggaatcaa agggaaaaag tacgaatcgg cctacaacgc ctcgaaggcc
481 ggggtgattt tgttgacgaa aaatgcagca ttggaatatg ggaagtttaa cattcgcgtc
541 aatgccattg caccgggggt cattgatacg aacatcatca cgccgtggaa acaagatgag
601 cgcaaarggc cgatcatttc gaaagcgaac gccctcggcc gcatcggcac gccagaggaa
661 gtggcgaacg cggtgttgtt tttggcgtcc gatgaagcgt cgtttatcac cggcgcgaca
721 ttgtcggtcg acggcgggcg gctgacgttt tag
```

Geobacillus thermodenitrificans DSM 465 nucleic acid sequence synthetic gene
SEQ ID NO: 10

```
  1 atgcgcctga aagggaaagc ggcaattgtg acgggtggcg ccagcggcat cggccgcgcg
 61 actgcgatcc gttttgcaga gagggtgcg aaagttgccg ttagcgacat taacgaggaa
121 ggcggtgagg aaaccgttcg cctgatccgt gaaaaggcg gtgaggcaat cttcgtgcag
181 acggatgtgg ccgactcaaa acaggtatct cgtctgattc agaccgcgat cgacgcgttt
241 ggtggcctgc acatcctgtt caataacgcc ggcattggcc atagcgaagt gcgtagtact
301 gatctgagcg aggaagagtg ggatcgcgtg attaacgtga acctgaaagg tgtgtttctg
361 ggtattaagt atgcagtccc tgttatgaaa cagtgtgcg gtggtgcgat tgtgaatacc
421 tctagtctgt tgggaatcaa agggaaaaag tatgaatcgg cctacaacgc atcgaaagcc
481 ggcgtcatcc tgctgaccaa aaatgcggcc ctggagtatg gcaagttcaa tattcgtgtc
541 aacgcgatcg ctccaggcgt tatcgatacc aacatcatta ccgtggaa gcaagatgaa
601 cgcaagtggc cgattatctc caaagctaat gcgctgggcc gtatcggtac gccggaagaa
661 gtggctaatg cggttctgtt tctggcaagc gacgaagcga gctttattac gggtgcaacc
721 ctctccgtag atgcgggcgg gttaaccttc taa
```

Chloroflexus auratiacus DSMZ 635 protein sequence carbonyl reductase
SEQ ID NO: 11

```
  1 meppfigkva lvtgaaagig rasalafare gakvvvadvn veggeetial craIntdamf
 61 vrcdvsqrde verlialavd tfgridfahn nagiegvqam ladypeevwd rvieinlkgv
121 wlcmkyeirh mlkqgggaiv ntssvaglag srgvsayvas khgivgitka aaleyarngi
181 rvnaicpgti htamidrftq gdpqllaqfa egepigrlgs peevanaviw lcsdkasfvt
241 gatlavdggr la
```

Chloroflexus auratiacus DSMZ 635 nucleic acid sequence carbonyl reductase
SEQ ID NO: 12

```
  1 atggagccac ctttcattgg aaggttgcg ctggtcaccg gcgcagcagc cggtattggt
 61 cgtgcttcag cactggcgtt tgcccgtgag ggtgccaagg ttgtcgttgc tgatgtgaat
121 gtcgagggcg gggaagagac gattgcgctg tgtcgggctt gaataccga tgcaatgttc
181 gtgcgttgtg atgtttcgca acgcgatgaa gtggagcgat taattgctct ggcagttgac
241 acgttcggtc ggatcgactt tgcgcacaac aacgccggga ttgaaggcgt gcaggcaatg
301 ctggccgatt atcccgaaga ggtctgggat cgggtgatcg agatcaacct caagggggtc
361 tggttgtgta tgaagtacga aatccggcac atgctcaagc agggtggcg tgcgattgtg
421 aatacctcat ccgtcgccgg tctggccgga tcacgtggga tttcggcgta tgtagccagc
481 aagcacggta ttgtgggtat taccaaagcg gcagcccttg agtatgcgcg taacggtatt
541 cgtgtcaacg caatctgtcc aggtacgatt catactgcga tgatcgaccg ctttacccag
601 ggtgatcccc aactgcttgc ccagttcgct gagggtgaac cgattggtcg gctcggctcg
661 cctgaagagg tcgccaatgc ggtgatctgg ctctgctcag ataaggcttc gtttgtgacc
721 ggagcgacac tggcggttga tggtggccgc tggcgtaa
```

Chloroflexus auratiacus DSMZ 635 nucleic acid sequence synthetic gene
SEQ ID NO: 13

```
  1 atggagcccc catttatcgg gaaagttgcg ttagttacgg gggcagcggc agggatcggt
 61 agggcgagtg ccctggcgtt tgctagagaa ggggccaagg tcgttgtggc agacgttaac
121 gtagagggtg gcgaagagac aattgctta tgcagagctc tcaacactga tgccatgttc
181 gtccgctgtg atgtgtcaca gcgagacgaa gtcgaaaggc taatcgccct agcggtagac
241 acattcggcc gtattgactt tgctcataat aacgcgggca tagagggagt acaagcaatg
```

-continued

```
301 ttggctgact atcctgagga agtatgggat cgagtaattg aaatcaatct caaggggtt
361 tggctgtgta tgaagtacga aataaggcac atgctcaagc aaggtggcgg agcgatcgta
421 aacactagct ctgtcgccgg tctagcagga tctcgggggg tttccgcata cgtcgcctcg
481 aaaacacggca ttgtagggat taccaaagct gcagcccttg agtatgcccg aaatggaata
541 agagtgaatg ctatctgccc aggcacaata catactgcaa tgatagatcg gtttacgcag
601 ggtgatccgc aacttttggc gcagttcgcc gaaggtgagc ctataggtcg ccttggtagc
661 ccggaagagg tcgctaatgc ggtgatttgg ttgtgttcag acaaagcaag tttcgtgacg
721 ggagctaccc tggcagtgga tggaggacgt ttagct
```

Candida magnoliae CBS 6396 protein sequence carbonyl reductase
SEQ ID NO: 14

```
  1 msatsnalit gasrgmgeat aiklalegys vtlasrgieq lnaikeklpi vkkgqqhyvw
 61 qldlsdieaa stfkgaplpa ssydvffsna gvvdfapfad qsetaqkdlf tvnllspval
121 tktivkaiad kpretpahii ftssivgirg vpnvavysat kgaidsfars larefgpkni
181 hvncvnpgtt rtemtkgvdl aafgdvpikg wievdaiada vlfliksknl tgqslvvdng
241 fgv
```

Candida magnoliae CBS 6396 nucleic acid sequence synthetic gene
SEQ ID NO: 15

```
  1 atgtctgcta cttcgaacgc tcttatcact ggtgccagcc gcggaatggg cgaggccaca
 61 gctattaagc ttgcccttga ggggtacagc gtcacccttg catcacgcgg tattgagcag
121 ctcaatgcca tcaaggaaaa actacccatc gtgaagaagg gccagcagca ctacgtttgg
181 cagctcgatc ttagtgacat cgaggcggct tccaccttca aggggggctcc tctgcctgcc
241 agcagctacg acgtgttctt cagcaacgcc ggtgtggtgg actttgctcc gttcgcagac
301 caaagcgaga ctgcgcaaaa ggacctgttc acggttaacc tgctgtcgcc tgttgcgttg
361 accaagacca ttgttaaggc catcgccgac aagccccgcg agacgcctgc tcacattatc
421 ttcacctcgt ccattgtcgg aattcgcggt gttcccaacg tggcggtcta cagcgccacc
481 aagggcgcga ttgacagctt gcgcgctcg cttgctcgtg agttcggtcc caagaacatc
541 cacgttaact gcgtgaaccc gggcacgacg cgcaccgaga tgacaaaggg cgttgatctc
601 gcggctttcg gcgatgttcc tatcaagggc tggatcgagg tcgatgcgat tgccgacgct
661 gtgctgtttt tgatcaagtc caagaacatc actggccagt cgctcgttgt tgacaacgga
721 ttcggtgttt aa
```

---

The invention claimed is:

1. A process for the enantioselective enzymatic reduction of a hydroxy ketone of general formula I

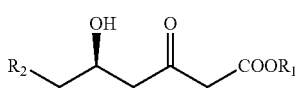

(I)

wherein $R_1 = C_1$-$C_6$ alkyl and $R_2 =$ —Cl, —CN, —OH, —H or $C_1$-$C_6$ alkyl, to a chiral diol of general formula II

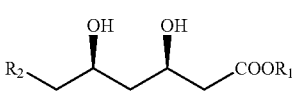

(II)

wherein $R_1$ and $R_2$ have the same meaning as in formula I, wherein the hydroxy ketone is reduced with an oxidoreductase in the presence of a cofactor, wherein the oxidoreductase
a) comprises the amino acid sequence of SEQ ID NO:8,
b) is encoded by the nucleic acid sequence SEQ ID NO:9 or SEQ ID NO:10, or
c) is encoded by a nucleic acid sequence which hybridizes to SEQ ID NO:9 or SEQ ID NO:10 under stringent conditions comprising washing with 0.1-2.0×SSC solution at 65° C.

2. The process according to claim 1, wherein the cofactor is continuously reduced with a co-substrate.

3. The process according to claim 1, wherein NAD(P)H is used as a cofactor.

4. The process according to claim 2, wherein at least one member selected from the group consisting of 2-propanol, 2-butanol, 2-pentanol, 4-methyl-2-pentanol, 2-heptanol and 2-octanol is used as the co-substrate.

5. The process according to claim 1, wherein the hydroxy ketone is used in an amount of from 5 to 50% by weight based on the total reaction volume.

6. The process according to claim 1, wherein at least one member selected from the group consisting of tert. butyl (5R)-6-cyano-5-hydroxy-3-oxohexanoate, tert. butyl (5S)-6-chloro-5-hydroxy-3-oxohexanoate and tert. butyl (5S)-5,6-dihydroxy-3-oxohexanoate is used as the hydroxy ketone of general formula (I).

7. The process according to claim 1, wherein the TTN (total turn over number=mol of reduced hydroxy ketone/mol of cofactor used) is $\geq 10^3$.

8. The process according to claim 1, wherein the process is carried out in an aqueous organic two-phase system.

9. The process according to claim 1, wherein, in addition, at least one organic solvent selected from the group consisting of diethyl ether, tertiary butyl methyl ether, diisopropyl ether, dibutyl ether, ethyl acetate, butyl acetate, heptane, hexane and cyclohexane is used.

10. A process for the enantioselective enzymatic reduction of a hydroxy ketone of general formula I

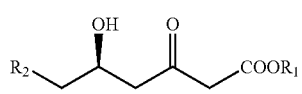

(I)

wherein $R_1 = C_1$-$C_6$ alkyl and $R_2 =$ —Cl, —CN, —OH, —H or $C_1$-$C_6$ alkyl, to a chiral diol of general formula II

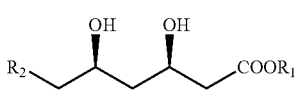

(II)

wherein $R_1$ and $R_2$ have the same meaning as in formula I, wherein the hydroxy ketone is reduced with an oxidoreductase in the presence of a cofactor,
wherein the oxidoreductase comprises the amino acid sequence SEQ ID NO:8.

11. The process according to claim 1, wherein the hydroxy ketone is used in an amount of from 8-40% by weight, based on the total reaction volume.

12. The process according to claim 1, wherein the hydroxy ketone is used in an amount of from 10-25% by weight, based on the total reaction volume.

13. A process for the enantioselective enzymatic reduction of a hydroxy ketone of general formula I

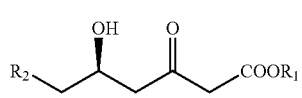

(I)

wherein $R_1 = C_1$-$C_6$ alkyl and $R_2 =$ —Cl, —CN, —OH, —H or $C_1$-$C_6$ alkyl, to a chiral diol of general formula II

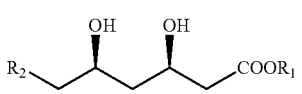

(II)

wherein $R_1$ and $R_2$ have the same meaning as in formula I, wherein the hydroxy ketone is reduced with an oxidoreductase in the presence of cofactor, wherein said oxidoreductase is encoded by a nucleic acid sequence which hybridizes to SEQ ID NO:9 or SEQ ID NO:10 under stringent conditions comprising washing with 0.1-2.0×SSC solution at 65° C.

* * * * *

SEQUENCE LISTING

<160> NUMBER OF SEQ ID NOS: 15

<210> SEQ ID NO 1
<211> LENGTH: 249
<212> TYPE: PRT
<213> ORGANISM: Rubrobacter xylanophilus

<400> SEQUENCE: 1

Met Leu Glu Gly Lys Val Ala Val Ile Thr Gly Ala Gly Ser Gly Ile
1               5                   10                  15

Gly Arg Ala Thr Ala Leu Arg Phe Ala Arg Glu Gly Ala Arg Val Val
            20                  25                  30

Val Ala Glu Leu Asp Glu Arg Gly Glu Glu Val Arg Glu Ile
        35                  40                  45

Leu Glu Ser Gly Gly Glu Ala Val Phe Val Arg Thr Asp Val Ser Glu
    50                  55                  60

Phe Glu Gln Val Glu Ala Ala Val Glu Arg Ala Val Glu Glu Tyr Gly
65                  70                  75                  80

Thr Leu Asp Val Met Phe Asn Asn Ala Gly Ile Gly His Tyr Ala Pro
                85                  90                  95

Leu Leu Glu His Asp Pro Glu His Tyr Asp Arg Val Val Arg Val Asn
            100                 105                 110

Gln Tyr Gly Val Tyr Gly Ile Leu Ala Ala Gly Arg Lys Met Ala
        115                 120                 125

Glu Leu Glu Asn Pro Gly Val Ile Ile Asn Thr Ala Ser Val Tyr Ala
    130                 135                 140

Phe Leu Ala Ser Pro Gly Val Ile Gly Tyr His Ala Ser Lys Gly Ala
145                 150                 155                 160
```

```
Val Lys Met Met Thr Gln Ala Ala Leu Glu Leu Ala Pro His Gly
            165                 170                 175
Ile Arg Val Val Ala Ile Ala Pro Gly Gly Val Asp Thr Pro Ile Ile
        180                 185                 190
Gln Gly Tyr Lys Asp Met Gly Leu Gly Glu Arg Leu Ala Arg Gly Gln
            195                 200                 205
Met Arg Arg Arg Leu Gln Thr Pro Glu Gln Ile Ala Gly Ala Val Val
    210                 215                 220
Leu Leu Ala Thr Glu Glu Ala Asp Ala Ile Asn Gly Ser Val Val Met
225                 230                 235                 240
Thr Asp Asp Gly Tyr Ala Glu Phe Lys
                245
```

<210> SEQ ID NO 2
<211> LENGTH: 750
<212> TYPE: DNA
<213> ORGANISM: Rubrobacter xylanophilus

<400> SEQUENCE: 2

```
atgctcgagg ggaaggtcgc ggtcatcacg ggggccggca gcggcatagg ccgggccacc      60
gcgctcaggt tcgcccgcga aggggcccgg gtggtcgtgg cggagctcga cgagcggagg     120
ggggaggagg tcgtccggga gatcctcgag tccggcgggg aggccgtctt cgtgaggacg     180
gacgtctcgg agttcgagca ggttgaggcc gccgtcgagc gcgccgtcga ggagtacggg     240
acgctggacg tcatgttcaa caacgccggc atcgggcact acgccccct gctggagcac     300
gacccggagc actacgaccg ggtggtccgg gtgaaccagt acggcgtcta ctacgggata     360
ctcgccgccg gcaggaagat ggccgagctg gagaaccccg gcgtgatcat caacaccgcc     420
tcggtctacg ctttcctggc ctcccccggt gtgatcggct atcacgcttc caaggggcg      480
gtgaagatga tgacccaggc cgcagccctg agctcgccc ccacggcat acgggtcgtc      540
gccatcgccc cgggcggggt ggacaccccg atcatccagg gctacaagga catgggcctc     600
ggtgagcggc tggcccgcgg ccagatgcgt cgcaggctcc agaccccga gcagatcgcc      660
ggcgccgtcg tcctgctcgc caccgaggag gcagacgcca taaacggctc ggtggtgatg     720
accgacgacg gctacgcgga gttcaagtaa                                      750
```

<210> SEQ ID NO 3
<211> LENGTH: 750
<212> TYPE: DNA
<213> ORGANISM: Artificial Sequence
<220> FEATURE:
<223> OTHER INFORMATION: synthetic modified DNA sequence coding for
      protein SEQ ID 1

<400> SEQUENCE: 3

```
atgctggaag gtaaagtggc agtcatcacc ggtgcaggca gcggcattgg cgtgccact       60
gcgctgcgtt ttgcgcgtga aggcgctcgc gtcgttgtgg ccgagctgga tgaacgtcgc     120
ggtgaggaag ttgtacgtga gattctggaa tctggcgggg aggccgtctt cgtgaggacg     180
gacgtctcgg agttcgagca ggttgaggcc gccgtcgagc gcgccgtcga ggagtacggg     240
acgctggacg tcatgttcaa caacgccggc atcgggcact acgccccct gctggagcac     300
gacccggagc actacgaccg ggtggtccgg gtgaaccagt acggcgtcta ctacgggata     360
ctcgccgccg gcaggaagat ggccgagctg gagaaccccg gcgtgatcat caacaccgcc     420
tcggtctacg ctttcctggc ctcccccggt gtgatcggct atcacgcttc caaggggcg      480
```

```
gtgaagatga tgacccaggc cgcagccctg gagctcgccc ccacggcat acgggtcgtc      540 gccatcgccc cgggcggggt ggacaccccg atcatccagg gctacaagga catgggcctc    600
ggtgagcggc tggcccgcgg ccagatgcgt cgcaggctcc agaccccga gcagatcgcc     660 ggcgccgtcg tcctgctcgc caccgaggag gcagacgcca taaacggctc ggtggtgatg    720
accgacgacg gctacgcgga gttcaagtaa                                      750
```

```
<210> SEQ ID NO 4
<211> LENGTH: 33
<212> TYPE: DNA
<213> ORGANISM: Artificial Sequence
<220> FEATURE:
<223> OTHER INFORMATION: synthetic oligonucleotide with restriction site
      for NdeI

<400> SEQUENCE: 4
gggaattcca tatgatgctc gagggaagg tcg                                   33

<210> SEQ ID NO 5
<211> LENGTH: 34
<212> TYPE: DNA
<213> ORGANISM: Artificial Sequence
<220> FEATURE:
<223> OTHER INFORMATION: synthetic oligonucleotide with restriction site
      for HindIII

<400> SEQUENCE: 5
cccaagctta ttacttgaac tccgcgtagc cgtc                                 34

<210> SEQ ID NO 6
<211> LENGTH: 30
<212> TYPE: DNA
<213> ORGANISM: Artificial Sequence
<220> FEATURE:
<223> OTHER INFORMATION: synthetic oligonucleotide with restriction site
      for NheI

<400> SEQUENCE: 6
cctagctagc atgctggaag gtaaagtggc                                      30

<210> SEQ ID NO 7
<211> LENGTH: 31
<212> TYPE: DNA
<213> ORGANISM: Artificial Sequence
<220> FEATURE:
<223> OTHER INFORMATION: synthetic oligonucleotide with restriction site
      for SphI

<400> SEQUENCE: 7
cacatgcatg cgaatgctcg aggggaaggt c                                    31

<210> SEQ ID NO 8
<211> LENGTH: 250
<212> TYPE: PRT
<213> ORGANISM: Geobacillus thermodenitrificans

<400> SEQUENCE: 8

Met Arg Leu Lys Gly Lys Ala Ala Ile Val Thr Gly Gly Ala Ser Gly
1               5                   10                  15

Ile Gly Arg Ala Thr Ala Ile Arg Phe Ala Glu Glu Gly Ala Lys Val
                20                  25                  30

Ala Val Ser Asp Ile Asn Glu Glu Gly Gly Glu Glu Thr Val Arg Leu
            35                  40                  45
```

```
Ile Arg Glu Lys Gly Gly Glu Ala Ile Phe Val Gln Thr Asp Val Ala
 50                  55                  60
Asp Ser Lys Gln Val Ser Arg Leu Val Gln Thr Ala Val Asp Ala Phe
 65                  70                  75                  80
Gly Gly Leu His Ile Leu Phe Asn Asn Ala Gly Ile Gly His Ser Glu
                 85                  90                  95
Val Arg Ser Thr Asp Leu Ser Glu Glu Trp Asp Arg Val Ile Asn
                100                 105                 110
Val Asn Leu Lys Gly Val Phe Leu Gly Ile Lys Tyr Ala Val Pro Val
            115                 120                 125
Met Lys Gln Cys Gly Gly Ala Ile Val Asn Thr Ser Ser Leu Leu
130                 135                 140
Gly Ile Lys Gly Lys Lys Tyr Glu Ser Ala Tyr Asn Ala Ser Lys Ala
145                 150                 155                 160
Gly Val Ile Leu Leu Thr Lys Asn Ala Ala Leu Glu Tyr Gly Lys Phe
                165                 170                 175
Asn Ile Arg Val Asn Ala Ile Ala Pro Gly Val Ile Asp Thr Asn Ile
            180                 185                 190
Ile Thr Pro Trp Lys Gln Asp Glu Arg Lys Trp Pro Ile Ile Ser Lys
        195                 200                 205
Ala Asn Ala Leu Gly Arg Ile Gly Thr Pro Glu Glu Val Ala Asn Ala
210                 215                 220
Val Leu Phe Leu Ala Ser Asp Glu Ala Ser Phe Ile Thr Gly Ala Thr
225                 230                 235                 240
Leu Ser Val Asp Gly Gly Leu Thr Phe
                245                 250

<210> SEQ ID NO 9
<211> LENGTH: 753
<212> TYPE: DNA
<213> ORGANISM: Geobacillus thermodenitrificans

<400> SEQUENCE: 9
atgaggctaa aaggaaaagc ggcgattgtc accggcggcg cgagcggcat cggccgggcg    60
acggcgattc gctttgcgga agaaggcgcc aaagtggcgg tgagcgacat caatgaggaa   120 ggagggaag aaacggtccg cctgattcgg gaaaaggag gggaggcgat ttttgtccaa   180
acggacgtag ccgattccaa gcaagtgagc cgccttgtcc aaacggcggt tgatgccttt   240
ggcggcctac atattctctt taacaatgcc ggcatcggcc attcggaagt gcggagcacc   300
gacttgtctg aagaagagtg ggaccgggtc atcaacgtta atttgaaagg agtgttcctt   360
ggcatcaaat acgcggtgcc cgtgatgaag caatgcggtg gcggggccat tgtcaacaca   420
tcgagcctgc ttggaatcaa aggaaaaaag tacgaatcgg cctacaacgc ctcgaaggcc   480
ggggtgattt tgttgacgaa aaatgcagca ttggaatatg gaagtttaa cattcgcgtc   540 aatgccattg caccgggggt cattgatacg aacatcatca cgccgtggaa acaagatgag   600
cgcaaatggc cgatcatttc gaaagcgaac gccctcggcc gcatcgggac gccagaggaa   660
gtggcgaacg cggtgttgtt tttggcgtcc gatgaagcgt cgtttatcac cggcgcgaca   720
ttgtcggtcg acggcggcgg gctgacgttt tag                                753

<210> SEQ ID NO 10
<211> LENGTH: 753
<212> TYPE: DNA
<213> ORGANISM: Artificial Sequence
<220> FEATURE:
```

<223> OTHER INFORMATION: synthetic modified DNA sequence coding for
      protein SEQ ID 8

<400> SEQUENCE: 10

```
atgcgcctga aagggaaagc ggcaattgtg acgggtggcg ccagcggcat cgggcgcgcg      60
actgcgatcc gttttgcaga agagggtgcg aaagttgccg ttagcgacat taacgaggaa     120
ggcggtgagg aaaccgttcg cctgatccgt gaaaaggcg gtgaggcaat cttcgtgcag      180
acggatgtgg ccgactcaaa acaggtatct cgtctggttc agaccgcggt cgacgcgttt     240
ggtggcctgc acatcctgtt caataacgcc ggcattggcc atagcgaagt cgtagtact     300
gatctgagcg aggaagagtg ggatcgcgtg attaacgtga acctgaaagg tgtgtttctg     360
ggtattaagt atgcagtccc tgttatgaaa cagtgtggcg tggtgcgat tgtgaatacc      420
tctagtctgt tgggaatcaa agggaaaaag tatgaatcgg cctacaacgc atcgaaagcc     480
ggcgtcatcc tgctgaccaa aaatgcggcc ctggagtatg caagttcaa tattcgtgtc      540
aacgcgatcg ctccaggcgt tatcgatacc aacatcatta caccgtggaa gcaagatgaa     600
cgcaagtggc cgattatctc caaagctaat gcgctgggcc gtatcggtac gccggaagaa     660
gtggctaatg cggttctgtt tctggcaagc gacgaagcga gctttattac gggtgcaacc     720
ctctccgtag atggggggcgg gttaaccttc taa                                 753
```

<210> SEQ ID NO 11
<211> LENGTH: 252
<212> TYPE: PRT
<213> ORGANISM: Chloroflexus aurantiacus

<400> SEQUENCE: 11

```
Met Glu Pro Pro Phe Ile Gly Lys Val Ala Leu Val Thr Gly Ala Ala
1               5                   10                  15

Ala Gly Ile Gly Arg Ala Ser Ala Leu Ala Phe Ala Arg Glu Gly Ala
            20                  25                  30

Lys Val Val Val Ala Asp Val Asn Val Glu Gly Gly Glu Glu Thr Ile
        35                  40                  45

Ala Leu Cys Arg Ala Leu Asn Thr Asp Ala Met Phe Val Arg Cys Asp
    50                  55                  60

Val Ser Gln Arg Asp Glu Val Glu Arg Leu Ile Ala Leu Ala Val Asp
65                  70                  75                  80

Thr Phe Gly Arg Ile Asp Phe Ala His Asn Asn Ala Gly Ile Glu Gly
                85                  90                  95

Val Gln Ala Met Leu Ala Asp Tyr Pro Glu Glu Val Trp Asp Arg Val
            100                 105                 110

Ile Glu Ile Asn Leu Lys Gly Val Trp Leu Cys Met Lys Tyr Glu Ile
        115                 120                 125

Arg His Met Leu Lys Gln Gly Gly Ala Ile Val Asn Thr Ser Ser
    130                 135                 140

Val Ala Gly Leu Ala Gly Ser Arg Gly Val Ser Ala Tyr Val Ala Ser
145                 150                 155                 160

Lys His Gly Ile Val Gly Ile Thr Lys Ala Ala Ala Leu Glu Tyr Ala
                165                 170                 175

Arg Asn Gly Ile Arg Val Asn Ala Ile Cys Pro Gly Thr Ile His Thr
            180                 185                 190

Ala Met Ile Asp Arg Phe Thr Gln Gly Asp Pro Gln Leu Leu Ala Gln
        195                 200                 205
```

```
Phe Ala Glu Gly Glu Pro Ile Gly Arg Leu Gly Ser Pro Glu Glu Val
    210                 215                 220

Ala Asn Ala Val Ile Trp Leu Cys Ser Asp Lys Ala Ser Phe Val Thr
225                 230                 235                 240

Gly Ala Thr Leu Ala Val Asp Gly Gly Arg Leu Ala
                245                 250

<210> SEQ ID NO 12
<211> LENGTH: 759
<212> TYPE: DNA
<213> ORGANISM: Chloroflexus aurantiacus

<400> SEQUENCE: 12
atggagccac ctttcattgg aaggttgcg  ctggtcaccg gcgcagcagc cggtattggt     60
cgtgcttcag cactggcgtt tgcccgtgag gtgccaagg  ttgtcgttgc tgatgtgaat    120
gtcgagggcg gggaagagac gattgcgctg tgtcgggctt gaataccga  tgcaatgttc    180 gtgcgttgtg atgtttcgca acgcgatgaa gtggagcgat taattgctct ggcagttgac    240
acgttcggtc ggatcgactt tgcgcacaac aacgccggga ttgaaggcgt gcaggcaatg    300
ctggccgatt atcccgaaga ggtctgggat cgggtgatcg agatcaacct caaaggggtc    360
tggttgtgta tgaagtacga atccggcac  atgctcaagc agggtggcgg tgcgattgtg    420
aatacctcat cggtcgccgg tctggccgga tcacgtggcg tttcggcgta tgtagccagc    480
aagcacggta ttgttggtat taccaaagcg gcagcccttg agtatgcgcg taacggtatt    540
cgtgtcaacg caatctgtcc aggtacgatt catactgcga tgatcgaccg ctttacccag    600
ggtgatcccc aactgcttgc ccagttcgct gagggtgaac cgattggtcg gctcggctcg    660
cctgaagagg tcgccaatgc ggtgatctgg ctctgctcag ataaggcttc gtttgtgacc    720
ggagcgacac tggcggttga tggtggccgc ctggcgtaa                           759

<210> SEQ ID NO 13
<211> LENGTH: 756
<212> TYPE: DNA
<213> ORGANISM: Artificial Sequence
<220> FEATURE:
<223> OTHER INFORMATION: synthetic modified DNA sequence coding for
      protein SEQ ID 11

<400> SEQUENCE: 13
atggagcccc catttatcgg aaagttgcg  ttagttacgg gggcagcggc agggatcggc     60
agggcgagtg ccctggcgtt tgctagagaa ggggccaagg tcgttgtggc agacgttaac    120
gtagagggtg gcgaagagac aattgcttta tgcagagctc tcaacactga tgccatgttc    180
gtccgctgtg atgtgtcaca gcgagacgaa gtcgaaaggc taatcgccct agcggtagac    240
acattcggcc gtattgactt tgctcataat aacgcgggca tagagggagt acaagcaatg    300
ttggctgact atcctgagga agtatgggat cgagtaattg aaatcaatct caaggggtt    360 tggctgtgta tgaagtacga ataaggcac  atgctcaagc aaggtggcgg agcgatcgta    420
aacactagct ctgtcgccgg tctagcagga tctcggggg  tttccgcata cgtcgcctcg    480
aaacacggca ttgagggat  taccaaagct gcagcccttg agtatgcccg aaatggaata    540
agagtgaatg ctatctgccc aggcacaata catactgcaa tgatagatcg gtttacgcag    600
ggtgatccgc aacttttggc gcagttcgcc gaaggtgagc ctataggtcg ccttggtagc    660
ccggaagagg tcgctaatgc ggtgatttgg ttgtgttcag acaaagcaag tttcgtgacg    720
ggagctaccc tggcagtgga tggaggacgt ttagct                              756
```

<210> SEQ ID NO 14
<211> LENGTH: 243
<212> TYPE: PRT
<213> ORGANISM: Candida magnoliae

<400> SEQUENCE: 14

Met Ser Ala Thr Ser Asn Ala Leu Ile Thr Gly Ala Ser Arg Gly Met
1               5                   10                  15

Gly Glu Ala Thr Ala Ile Lys Leu Ala Leu Glu Gly Tyr Ser Val Thr
            20                  25                  30

Leu Ala Ser Arg Gly Ile Glu Gln Leu Asn Ala Ile Lys Glu Lys Leu
        35                  40                  45

Pro Ile Val Lys Lys Gly Gln Gln His Tyr Val Trp Gln Leu Asp Leu
    50                  55                  60

Ser Asp Ile Glu Ala Ala Ser Thr Phe Lys Gly Ala Pro Leu Pro Ala
65                  70                  75                  80

Ser Ser Tyr Asp Val Phe Phe Ser Asn Ala Gly Val Val Asp Phe Ala
                85                  90                  95

Pro Phe Ala Asp Gln Ser Glu Thr Ala Gln Lys Asp Leu Phe Thr Val
            100                 105                 110

Asn Leu Leu Ser Pro Val Ala Leu Thr Lys Thr Ile Val Lys Ala Ile
        115                 120                 125

Ala Asp Lys Pro Arg Glu Thr Pro Ala His Ile Ile Phe Thr Ser Ser
    130                 135                 140

Ile Val Gly Ile Arg Gly Val Pro Asn Val Ala Val Tyr Ser Ala Thr
145                 150                 155                 160

Lys Gly Ala Ile Asp Ser Phe Ala Arg Ser Leu Ala Arg Glu Phe Gly
                165                 170                 175

Pro Lys Asn Ile His Val Asn Cys Val Asn Pro Gly Thr Thr Arg Thr
            180                 185                 190

Glu Met Thr Lys Gly Val Asp Leu Ala Ala Phe Gly Asp Val Pro Ile
        195                 200                 205

Lys Gly Trp Ile Glu Val Asp Ala Ile Ala Asp Ala Val Leu Phe Leu
    210                 215                 220

Ile Lys Ser Lys Asn Ile Thr Gly Gln Ser Leu Val Val Asp Asn Gly
225                 230                 235                 240

Phe Gly Val

<210> SEQ ID NO 15
<211> LENGTH: 732
<212> TYPE: DNA
<213> ORGANISM: Candida magnoliae

<400> SEQUENCE: 15
atgtctgcta cttcgaacgc tcttatcact ggtgccagcc gcggaatggg cgaggccaca      60
gctattaagc ttgcccttga ggggtacagc gtcacccttg catcacgcgg tattgagcag     120
ctcaatgcca tcaaggaaaa actacccatc gtgaagaagg ccagcagca ctacgtttgg      180 cagctcgatc ttagtgacat cgaggcggct tccaccttca gggggctcc tctgcctgcc      240 agcagctacg acgtgttctt cagcaacgcc ggtgtggtgg actttgctcc gttcgcagac     300
caaagcgaga ctgcgcaaaa ggacctgttc acggttaacc tgctgtcgcc tgttgcgttg     360
accaagacca ttgttaaggc catcgccgac aagcccgcg agacgcctgc tcacattatc      420
ttcacctcgt ccattgtcgg aattcgcggt gttcccaacg tggcggtcta cagcgccacc     480

```
aagggcgcga ttgacagctt tgcgcgctcg cttgctcgtg agctcggtcc caagaacatc    540
cacgttaact gcgtgaaccc gggcacgacg cgcaccgaga tgacaaaggg cgttgatctc    600
gcggctttcg gcgatgttcc tatcaagggc tggatcgagg tcgatgcgat tgccgacgct    660
gtgctgtttt tgatcaagtc caagaacatc actggccagt cgctcgttgt tgacaacgga    720
ttcggtgttt aa                                                       732
```